US00PP18247P3

(12) United States Plant Patent
Parsons et al.

(10) Patent No.: US PP18,247 P3
(45) Date of Patent: Nov. 27, 2007

(54) BERMUDAGRASS PLANT NAMED 'PREMIER'

(50) Latin Name: *Cynodon dacytlon*
Varietal Denomination: Premier

(76) Inventors: Donald La Verne Parsons, 22392 Sunlight Creek, Lake Forest, CA (US) 92630; Virginia Gail Lehman, 811 Mountain River Dr., Lebanon, OR (US) 97355

( * ) Notice: Subject to any disclaimer, the term of this patent is extended or adjusted under 35 U.S.C. 154(b) by 599 days.

(21) Appl. No.: 10/768,091

(22) Filed: Feb. 2, 2004

(65) Prior Publication Data

US 2005/0172377 P1 Aug. 4, 2005

(51) Int. Cl.
*A01H 5/00* (2006.01)

(52) U.S. Cl. ..... Plt./389

(58) Field of Classification Search ..... Plt./389
See application file for complete search history.

(56) References Cited

PUBLICATIONS

MPEP 609 [R–5] p. 1–4 (MPEP=Manual of Patent Examining Practice) USPTO.*

* cited by examiner

*Primary Examiner*—Anne Marie Grunberg
*Assistant Examiner*—Georgia Helmer
(74) *Attorney, Agent, or Firm*—Klarquist Sparkman, LLP

(57) ABSTRACT

An asexually reproduced variety of perennial bermudagrass with a unique combination of characters including fine blade width and medium internode length.

1 Drawing Sheet

Latin name of the genus and species of the plant claimed: The present invention relates to the genus and species *Cynodon dacytlon* (L.) Pers.
Variety denomination: 'Premier'.

BACKGROUND OF THE INVENTION

Field of Invention

The present invention relates to a new and distinct asexually reproduced variety of perennial bermudagrass *Cynodon dacytlon* (L.) Pers.

BRIEF SUMMARY OF THE INVENTION

This invention relates to a new and distinct perennial bermudagrass cultivar identified as 'Premier' bermudagrass (herein referred to as 'Premier'). The inventors, Donald Parsons and Virginia Lehman, discovered 'Premier' under cultivated conditions in a golf course fairway near Seal Beach, Calif. 'Premier' was identified as a distinctly different vegetative patch or segregated clonal plant differing by darker green leaf color from the suspected parental variety common Tifgreen (unpatented). The inventors asexually reproduced 'Premier' by taking vegetative cuttings of the plant material from the golf course including stolons and rhizomes, cutting the rhizomes and stolons into segments, each with a vegetative bud, and rooted them in potting media in a greenhouse near Parker, Tex.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Bermudagrass plant named 'Premier'.

BRIEF DESCRIPTIONS OF THE ILLUSTRATIONS

FIG. 1. Tiller of 'Premier' bermudagrass.

COMPLETE DESCRIPTION OF THE VARIETY

'Premier' was characterized in greenhouse and field conditions. 'Premier' is a unique variety of bermudagrass (*Cynodon dacytlon* (L.) Pers). that was discovered under cultivated conditions in a gold course fairway near Seal Beach, Calif. 'Premier' was identified in the field as having a darker green leaf color than its suspected parent 'Tifgreen'. The golf course fairway was located in USDA Plant Hardiness Zone 9. 'Premier' was propagated by the inventors under field and greenhouse conditions in Parker, Tex. by cutting of rhizomes and stolons, rooting them in soil, and planting of the rooted material to provide planting stock for studying performance and for comparison of morphological characters after propagation. 'Premier' has been propagated by rhizomes, stolons, tillers, and sod. Asexually reproduced plants of 'Premier' have remained stable and true to type through successive generations of propagation. No seedling establishment from 'Premier' has been noticed in either greenhouse or field studies.

'Premier' is a perennial bermudagrass that spreads by both stolons and rhizomes. Characteristics of 'Premier' measured in 2003 were taken from plants that were approximately 9 months in age. The greenhouse was located near Lebanon, Oreg., with a nighttime low temperature of 50 degrees F., and daytime high of 80 degrees F., and a minimum soil temperature of 60 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'Premier' has a finer leaf texture than the suspected parent 'Tifgreen' (Table 1) when measured under greenhouse conditions in Lebanon, Oreg. 'Premier' has few surface leaf (1–5) hairs compared to the variety Tifgreen which has no leaf hairs. The hairs at the mouth of the sheath of 'Premier' are longer than 'Tifway' and 'Tifgreen' (Table 3). No seeds of 'Premier' have developed; no seedlings have been noted in the field studies. The inflorescences produced in the greenhouse have consisted of empty florets and no seed has been formed.

'Premier' has not shown any susceptibility in tests to date in the Aubrey, Tex. test production site to the diseases and insects common to the bermudagrass genus. 'Premier' has shown good turfgrass performance and temperature adaptation when tested in Dallas, Tex. (Table 4), and as far north as Aubrey, Tex. USDA zone 8A, which would extend the area of adaptation for 'Premier' in a line from South-Central Alabama across central Arkansas through North Central Texas, across New Mexico and Arizona to Los Angeles in an East/West line and on a North/South line from North central Texas south through Mexico. 'Premier' will be limited only by winter survival in colder regions, and is undergoing further research to determine the most northern area of survival at this time. 'Premier' is similar to most medium to fine textured bermudagrasses in water use demands as shown in production situations, and will be limited by adequate precipitation in drier to arid regions. 'Premier' is adapted from sandy to heavier loam soil textures and from slightly acid to slightly alkaline soil pH.

TABLE 1

Leaf blade widths and lengths and texture class of selected bermudagrass cultivars, measured under greenhouse conditions in Lebanon, OR, 2003.

| Variety | Width, 2nd youngest stolon leaf mm | Length, 2nd youngest stolon leaf cm | Length, 3rd panicle leaf cm | Width, 3rd panicle leaf mm | Leaf Texture Class |
|---|---|---|---|---|---|
| OR2002 | 2.15 | 2.24 | 2.29 | 1.58 | Medium |
| Tifgreen | 2.77 | 2.79 | 2.01 | 2.11 | Medium |
| Tifway | 2.37 | 3.01 | 2.22 | 1.77 | Medium |

TABLE 2

Inflorescence and leaf characters of selected bermudagrass cultivars, measured under greenhouse conditions in Lebanon, OR 2003.

| Variety | Number panicle branches cm | Flag leaf width mm | Flag leaf length cm | Leaf Sheath Length, Flag Leaf mm | Leaf Sheath Length, 4th Youngest Vegetative Leaf mm |
|---|---|---|---|---|---|
| 'Premier' | 3.50 | 0.89 | 0.61 | 2.9 | 1.9 |
| 'Tifgreen' | 3.38 | 1.26 | 0.84 | 3.1 | 1.8 |
| 'Tifway' | 3.00 | 0.91 | 0.65 | 3.3 | 2.4 |

TABLE 3

Sheath hair length and stolon internode length measurements of selected bermudagrass cultivars, measured under greenhouse conditions in Lebanon, OR, 2003

| Variety | Hair length, mouth of sheath mm | Stolon Internode length, node 2-3 cm | Stolon Internode length, node 3-4 cm |
|---|---|---|---|
| 'Premier' | 2.35 | 4.63 | 5.19 |
| 'Tifgreen' | 2.06 | 3.77 | 3.60 |
| 'Tifway' | 2.12 | 5.73 | 5.33 |

TABLE 4

Turf quality characters, Dallas, TX, 2003.

| Genetic Color | Spring Greenup | Leaf texture | Quality May | Variety |
|---|---|---|---|---|
| 7.33 | 5.67 | 7.67 | 6.33 | Premier |
| 7.57 | 6.00 | 8.00 | 5.67 | Tifway |
| 7.33 | 5.87 | 7.00 | 6.67 | Celebration |
| 7.00 | 5.00 | 6.33 | 6.00 | Tift No. 1 |
| 6.57 | 4.00 | 6.00 | 4.00 | Az. Common |
| 6.67 | 3.33 | 6.00 | 5.00 | NM Sahara |
| 7.00 | 6.00 | 7.33 | 6.33 | Midlawn |
| 7.67 | 5.33 | 7.67 | 6.00 | Tifsport |
| 7.67 | 5.67 | 6.33 | 5.00 | MS-Choice |
| 0.75 | 1.00 | 0.70 | 1.30 | LBD |

| Quality June | Quality July | Quality August | Mean Quality | Variety |
|---|---|---|---|---|
| 6.33 | 7.00 | 7.00 | 5.47 | Premier |
| 5.67 | 7.00 | 6.33 | 5.17 | Tifway |
| 5.67 | 6.67 | 6.00 | 5.03 | Celebration |
| 5.67 | 6.00 | 5.57 | 5.19 | Tift No. 1 |
| 4.67 | 5.00 | 5.00 | 4.14 | Az. Common |
| 5.00 | 6.00 | 5.33 | 4.53 | NM Sahara |
| 6.33 | 6.67 | 7.00 | 5.36 | Midlawn |
| 6.33 | 7.00 | 7.00 | 5.08 | Tifsport |
| 6.33 | 6.33 | 6.33 | 4.64 | MS-Choice |
| 0.77 | 0.66 | 0.71 | | LBD |

| Spring Density | Summer Density | Fall Density | Dec. Color | Variety |
|---|---|---|---|---|
| 5.00 | 8.00 | 7.67 | 2.67 | Premier |
| 5.00 | 7.67 | 8.00 | 5.00 | Tifway |
| 5.33 | 8.00 | 7.33 | 3.00 | Celebration |
| 5.33 | 7.67 | 7.33 | 3.33 | Tift No. 1 |
| 3.67 | 7.00 | 7.00 | 2.00 | Az. Common |
| 4.67 | 7.00 | 7.00 | 1.33 | NM Sahara |
| 6.00 | 7.67 | 8.00 | 3.67 | Midlawn |
| 4.00 | 8.00 | 7.67 | 5.00 | Tifsport |
| 4.33 | 7.67 | 7.33 | 3.00 | MS-Choice |
| 1.79 | 0.53 | 1.21 | 1.00 | LBD |

COMPLETE BOTANICAL DESCRIPTION OF THE VARIETY

Origin: 'Premier' is a cultivar of a single clone of bermudagrass discovered under cultivated conditions in a Seal Beach, Calif. golf course fairway of 'Tifgreen' bermudagrass.

Classification: *Cynodon dacytlon* (L.) Pers.

Growth habit: 'Premier' is a perennial plant hat spreads by stolons and rhizomes and produces a dense, fine textured turfgrass. The inflorescence of 'Premier' is a panicle, with branches originating from a common center.

Leaf blade: fold in the bud, slightly concave surface versus Tifgreen and Tifway, both of which have flat leaves.

Leaf blade pubescence: Adaxial leaf surface have very few, short (1–5) hairs versus Tifway with many hairs on adaxial surface; hairs mostly absent on abaxial leaf surface.

Leaf sheath pubescence: present with very short hairs versus Tifgreen with no pubescence.

Leaf blade margin: rough versus Tifgreen with slightly rough margin.

Leaf blade veins: obscure.

Leaf ligule hairs; present, very short.

Leaf blade flexibility (softness): Stiff versus Tifgreen: soft; Tifway; medium stiffness.

Vegetative leaf, fourth youngest vegetative leaf:

*Blade length mean.*—2.46 cm

*Blade width mean.*—2.15 mm

*Sheath length mean.*—1.9 cm.

Stolon internode length, node 2–3: 4.63 cm.

Stolon internode length, node 3–4: 5.19 cm.

Stolon internode width, node 2–3: 0.89×1.02 mm.

Stolon internode width, node 3–4: 0.99×1.07 mm.

Inflorescence characters:

*Length of flowering stem from lower node to panicle center.*—7.74; Tifgreen: 14.14 cm.

*Internode length from flag leaf to 2$^{nd}$ internode below flag.*—4.73 cm.

*Culm width, stem thickness, base of floral area.*—0.47 mm; Tifway: 0.54 mm.

*Node thickness, node below flag leaf.*—0.65 mm.

Mature plant height, including inflorescence: 10.8; Tifgreen: 15.23 cm.

Color Notations, vegetative characters, based on The R.H.S. Colour Chart (light quality, photoperiod, and general growth of the plants affect color notations):

*Leaf blade color adaxial leaf surface.*—137B green.

*Stolon color.*—59A red purple and 145B yellow green.

Color Notations, floral characters, based on The R.H.S. Colour Chart (light quality, photoperiod, and general growth of the plants affect color notations):

*Stigma color.*—61A red-purple.

*Anther color.*—5C yellow.

Turf quality (rated 1–9, 9 best): 8; 'Tifgreen': 7.

Turf color (rated 1–9, 9 best): 7; 'Tifgreen': 6.

We claim:

1. A new and distinct variety of bermudagrass plant, substantially as described and illustrated herein.

* * * * *

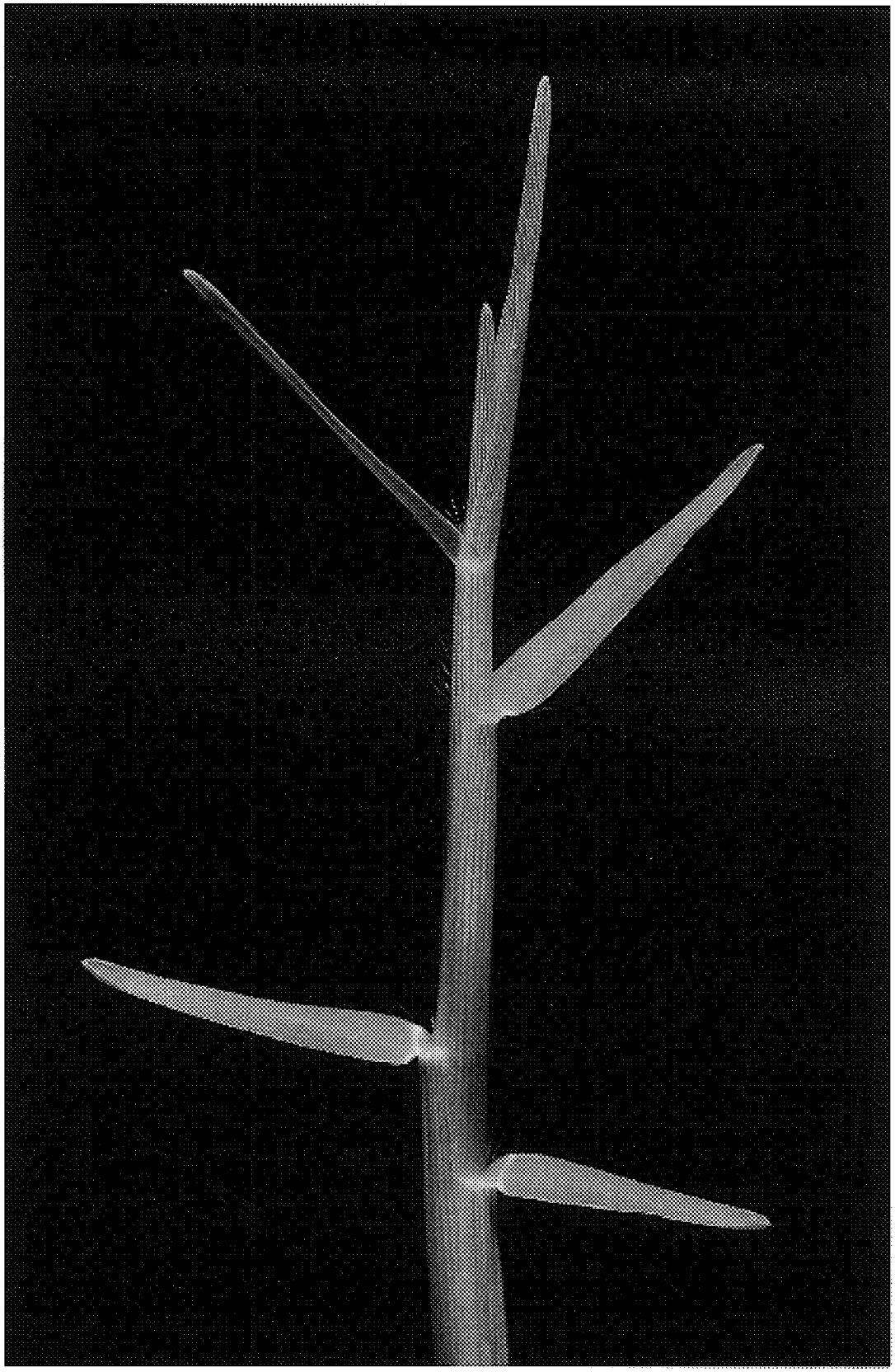

UNITED STATES PATENT AND TRADEMARK OFFICE

CERTIFICATE OF CORRECTION

PATENT NO. : PP 18,247 P3
APPLICATION NO. : 10/768091
DATED : November 27, 2007
INVENTOR(S) : Parsons and Lehman It is certified that error appears in the above-identified patent and that said Letters Patent is hereby corrected as shown below:

In the Specification:

Column 4, Table 4, the second entry in the column labeled “Genetic Color”, “7.57” should be --7.67--.

Column 4, Table 4, the second entry in the column labeled “Spring Greenup”, “6.00” should be --5.00--.

Column 4, Table 4, the third entry in the column labeled “Spring Greenup”, “5.87” should be --5.67--.

Column 4, Table 4, the ninth entry in the column labeled “Quality May”, “5.00” should be --6.00--.

Column 4, Table 4, the tenth entry in the column labeled “Variety”, all three occurrences of “LBD” should be --LSD--.

Column 4, Table 4, the ninth entry in the column labeled “Quality June”, “6.33” should be --5.33--.

Column 4, Table 4, the sixth entry in the column labeled “Quality July”, “6.00” should be --5.00--.

Column 4, Table 4, the fourth entry in the column labeled “Quality August”, “5.57” should be --5.67--.

Column 4, line 63, “hat” should be --that--.

Column 5, line 10, “hairs;” should be --hairs:--.

UNITED STATES PATENT AND TRADEMARK OFFICE

CERTIFICATE OF CORRECTION

PATENT NO. : PP 18,247 P3
APPLICATION NO. : 10/768091
DATED : November 27, 2007
INVENTOR(S) : Parsons and Lehman It is certified that error appears in the above-identified patent and that said Letters Patent is hereby corrected as shown below:

Column 5, line 12, “Tifway;” should be --Tifway:--.

Signed and Sealed this

Twenty-ninth Day of July, 2008

JON W. DUDAS
*Director of the United States Patent and Trademark Office*